United States Patent [19]
Lunsford

[11] Patent Number: 4,597,917
[45] Date of Patent: Jul. 1, 1986

[54] PORTABLE MEDICAL GAS WARMING SYSTEM

[76] Inventor: Kevin S. Lunsford, 8273 Community Dr., Manassas, Va. 22110

[21] Appl. No.: 486,484

[22] Filed: Apr. 19, 1983

[51] Int. Cl.$^4$ .................. B01F 3/04; A61M 16/16
[52] U.S. Cl. ............................ 261/153; 128/200.11; 128/203.26; 128/204.17; 261/121 R; 261/141; 261/DIG. 65
[58] Field of Search .............. 261/121 R, 141, 153, 261/DIG. 65; 126/263; 128/203.26, 204.17, 200.11, 202.26; 165/104.12; 422/120, 122, 123, 125, 187

[56] References Cited

U.S. PATENT DOCUMENTS

| | | | |
|---|---|---|---|
| 540,504 | 6/1895 | Madden | 128/204.17 |
| 1,094,301 | 4/1914 | Caine | 128/200.13 X |
| 1,483,620 | 2/1924 | Spinola | 128/200.11 |
| 2,553,878 | 5/1951 | Steven | 126/263 |
| 2,866,456 | 12/1958 | Lovy et al. | 128/205.24 |
| 3,565,068 | 2/1971 | Bickford | 128/202.26 X |
| 3,685,507 | 8/1972 | Donnelly | 126/263 |
| 3,725,153 | 4/1973 | Schroder et al. | 126/263 X |
| 3,733,008 | 5/1973 | Churchill et al. | 128/202.26 X |
| 3,834,385 | 9/1974 | Pekkarinen | 239/370 |
| 3,889,483 | 6/1975 | Donnelly | 126/263 X |
| 3,903,011 | 9/1975 | Donnelly | 126/263 X |
| 3,903,216 | 9/1975 | Allan et al. | 261/121 R X |
| 3,923,057 | 12/1975 | Chalon | 128/205.28 X |
| 3,929,128 | 12/1975 | Pekkarinen | 239/370 X |
| 3,942,510 | 3/1976 | Garrett | 126/263 |
| 3,955,931 | 5/1976 | Thompson | 128/202.26 X |
| 3,976,049 | 8/1976 | Yamashita et al. | 126/263 |
| 4,002,235 | 1/1977 | Donnelly | 126/263 X |
| 4,013,742 | 3/1977 | Lang | 261/153 X |
| 4,014,384 | 3/1977 | Marcus | 165/135 X |
| 4,255,157 | 3/1981 | Yamaguchi et al. | 126/263 X |
| 4,292,967 | 10/1981 | Pasternack | 422/123 X |
| 4,319,566 | 3/1982 | Hayward et al. | 128/203.16 X |
| 4,325,364 | 4/1982 | Evans | 128/204.17 X |
| 4,342,725 | 8/1982 | Collins | 422/120 X |

FOREIGN PATENT DOCUMENTS

| | | | |
|---|---|---|---|
| 2638277 | 3/1978 | Fed. Rep. of Germany | 128/204.17 |
| 81/03618 | 12/1981 | World Int. Prop. O. | 128/202.26 |
| 1540375 | 2/1979 | United Kingdom | 128/204.17 |

OTHER PUBLICATIONS

Weinel, Inc., J. E.; "Applinc Saving Breath Hypo-Thermia Systems"; Catalog No. 8A; pp. 56, 57; 1984.
Ron Servine, Mountaineering Medicine, Journal of Emergency Services, vol. 12, No. 7, 82 Edition, Jul. 1980.
Miles Julihn, An Emergency Revisited, Journal of Emergency Service, vol. 12, No. 2, 77 Edition, Feb. 1980.
R. H. LaRue, Cold Water Near-Drowning, Journal of Emergency Service, vol. 3, No. 6, 93 Edition, Jun. 1981.
Greg Gille, M. S., Looking the Other Way, Journal of Emergency Service, vol. 13, No. 3, 90 Edition, Mar. 1981.
Stan Bush, Beyond the Roadhead, Journal of Emergency Services, vol. 11, No. 9, 72 Edition, Sep. 1979.

Primary Examiner—Richard L. Chiesa
Attorney, Agent, or Firm—Parkhurst & Oliff

[57] ABSTRACT

A highly portable means for warming therapeutic gas to be administered to a patient which may also humidify the therapeutic gas. The apparatus includes means for passing the therapeutic gas through an area heated by a chemical reaction which requires no outside energy source. The heated area may comprise a liquid such as water which may optionally contain other therapeutic substances, resulting in both heating and humidifying of the therapeutic gas. The chemical heating means involves mixing two or more chemicals such as a liquid chemical and a dry chemical or atmospheric air and a dry chemical to produce an exothermic reaction. The apparatus is highly portable and may be carried, for instance, in ambulances, boats, aircraft, etc., as well as at medical facilities such as hospitals. The apparatus is lightweight, cheap to construct and economically disposable after use, thus avoiding the possibility of cross-contamination and avoiding any need for cleaning.

22 Claims, 6 Drawing Figures

PORTABLE MEDICAL GAS WARMING SYSTEM

BACKGROUND OF THE INVENTION

1. Field of the Invention

Warmed ari, oxygen, or other therapeutic gases are often required under circumstances in which bulky electrical heating apparatuses may not practically be used. For instance, accidental hypothermia (a condition in which the core body temperature drops below 35° C. (95° F.)) may occur as a result of accidental exposure to the cold in the outdoors, perhaps from immersion in cold water or mountain accidents. However, it can also occur in the heated indoors. Particularly susceptible persons are the elderly, infants, sportsmen and military personnel.

A traditional way of treating accidental hypothermia has been by rapid peripheral rewarming. However, this method often causes peripheral vasodilation which releases reservoirs of cooled, potentially acidic and high potassium blood to flow back to the body core, resulting in a drop in body core temperature of 0.25° C.–1.6° C. (0.5° F.–3° F.) about 30 minutes after rewarming has begun. This results in a possibility of ventricular fibrillation due to further cooling of the myocardium. Thus rapid peripheral rewarming of accidental hypothermia victims involves potential hazards which cannot be easily handled outside of a hospital environment.

Accordingly, more recent attempts have been made to rewarm hypothermic individuals by directly heating the body core rather than heating the periphery of the body. Hospital treatment of victims of hypothermia by core rewarming may involve peritoneal dialysis (introduction of warm saline solution into the abdominal cavity) or inhalation rewarming. Inhalation of warm, dry or water saturated air and/or oxygen provides small amounts of heat directly to the head, neck and thoracic core. Even the small amount of heat directly provided by this method results in very good rewarming with minimum afterdrop of core temperature without stimulating the return of cool peripheral blood which may have excessive acidity and potassium concentration.

Warm, moist air is also very useful for relieving larengectomy and tracheotomy patients, and to relieve asthmatic bronchial spasms.

As the need for such treatment often arises outside of the hospital environment and is best performed without delay, use of a device for performing such treatment which is conveniently portable is highly desirable.

2. Description of the Prior Art

As noted above, hospital treatment of hypothermia patients by means of inhalation rewarming has previously been attempted in the hospital environment. Devices for accomplishing this have generally involved large, bulky apparatus with external power sources which are portable, if at all, only in a very limited way. Exemplary of such a known device is that disclosed in U.S. Pat. No. 4,013,742 to Lang, in which a complex electrical heating system is used to heat a container of water through which a respiratory gas is bubbled. Earlier devices for heating inhalation gases, as disclosed in U.S. Pat. Nos. 540,504, 1,094,301 and 1,483,620 used such bulky and inconvenient means for heating the gases as burner flames and boiling water. More recently, as shown in U.S. Pat. No. 3,923,057 to Chalon, chemical means have been used to heat inhalation gases. However, even such means have until now required very bulky and non-portable apparatus such as that disclosed in the Chalon patent.

Some efforts have been directed in the art toward achieving a portable inhalation gas heating apparatus, as exemplified by U.S. Pat. No. 4,319,566 to Hayward et al. However, such devices as the Hayward et al device also require an external power source such as propane or battery-electric power to warm the inhalation gases, resulting in relatively high cost and limited portability.

SUMMARY OF THE INVENTION

The present invention is directed to a highly portable hand-held means for warming therapeutic gas to be administered to a patient. In a preferred embodiment, the apparatus will also humidify the therapeutic gas. The apparatus includes means for passing the therapeutic gas through an area heated by means of a chemical reaction which requires no outside energy source. In one embodiment, the heated area comprises a liquid such as water which may optionally contain other therapeutic subtances, resulting in both heating and humidifying of the therapeutic gas. The chemical heating means involves mixing two or more chemicals to produce an exothermic reaction. In one embodiment, a liquid chemical and a dry chemical may be mixed by breaking a frangible barrier therebetween; in another embodiment one of the chemicals comprises atmospheric air which is mixed with a dry chemical by selectively opening to the atmosphere the container holding the dry chemical.

The apparatus is highly portable and may be carried, for instance, in ambulances, boats, aircraft, etc., as well as at medical facilities such as hospitals. The apparatus is also lightweight, cheap to construct and economically disposable after use, thus avoiding the possibility of cross-contamination and avoiding any need for cleaning.

BRIEF DESCRIPTION OF THE DRAWINGS

In the Figures, the same numbers refer to corresponding parts of the various embodiments.

DESCRIPTION OF PREFERRED EMBODIMENTS

The present invention will hereunder be described with respect to certain exemplary embodiments thereof. However, the following description is not intended to be limiting with respect to the breadth of the appended claims, which embrace many variations upon the presently described invention which would be apparent to those of skill in this art in light of the present disclosure.

Figure 1:
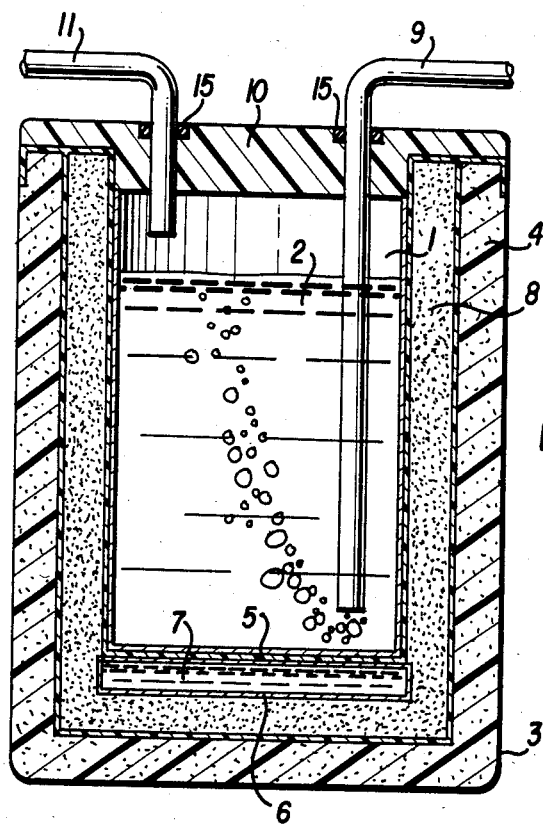
FIG. 1 is a side view of an embodiment of a portable medical gas warming system according to the invention.

In the embodiment shown in FIG. 1, a thermally conductive disposable container 1 (for instance, a commercially available container such as was mentioned in the Lang patent, supra) containing a sterile liquid such as water 2 may be inserted into a second disposable container 3 having a heat insulative outer wall 4 (which may for instance be formed from an insulative plastic material sold under the trademark "Styrofoam") and a strong plastic inner wall 5. Container 1 may be a standard water container presently used in non-portable prior art systems. Alternatively, outer container 3 may itself hold the liquid 2 without the need for a container 1 in such a disposable system. Between outer wall 4 and inner wall 5 are at least two compartments separated by a frangible membrane 6. The size and coextensiveness of these two compartments is determined by the nature of the chemicals therein and the amount of heat desired. The device should be so constructed as to acheive an outlet gas temperature of approximately 100°-110° F. (38°-43° C.), preferably approximately 104° F. (40° C.). In FIG. 1, compartment 7 contains a liquid activating chemical such as water and compartment 8 contains a dry chemical such as magnesium sulfate or another reactive liquid.

To activate the apparatus, pressure is applied to the strong plastic wall 5 near the frangible plastic membrane 6 to rupture said frangible membrane. This is most conveniently performed by means of finger pressure with the container 1 removed, although optionally a portion of container 1 can be so shaped as to allow the pressing of this container against the plastic wall 5 to result in fracturing of the frangible membrane 6. Alternatively, the outer container 3 may be so constructed as to allow fracturing of the frangible membrane by external pressure. However, safeguards would have to be included to avoid accidental fracturing of the membrane during handling. Upon rupturing of the frangible membrane 6, the mixture of the two chemicals brings about an exothermic reaction which heats the material in the container 1. A therapeutic gas is passed into the lower portion of the container 1 by means of conduit 9 which passes through lid 10 of the container 1. Lid 10 may alternatively fit with outer container 3 rather than inner container 1 in the case of a disposable outer container. Furthermore, the disposable container 3 may itself contain the liquid 2 instead of that liquid being held in a separate container. The inlet and outlet conduits pass through lid 10 in an airtight fashion, for instance past O-rings 15. The gas bubbles up through the liquid 2 in container 1, being heated and humidfied thereby, and is removed from the apparatus and carried to the patient by means of exit conduit 11. Inlet conduit 9 may be connected to a source of pressurized oxygen, air, etc. (not shown), while exit conduit 11 may lead to an inhalation mask, tent, etc. (not shown) through which the treated gas is provided to the patient for inhalation.

Figure 2:
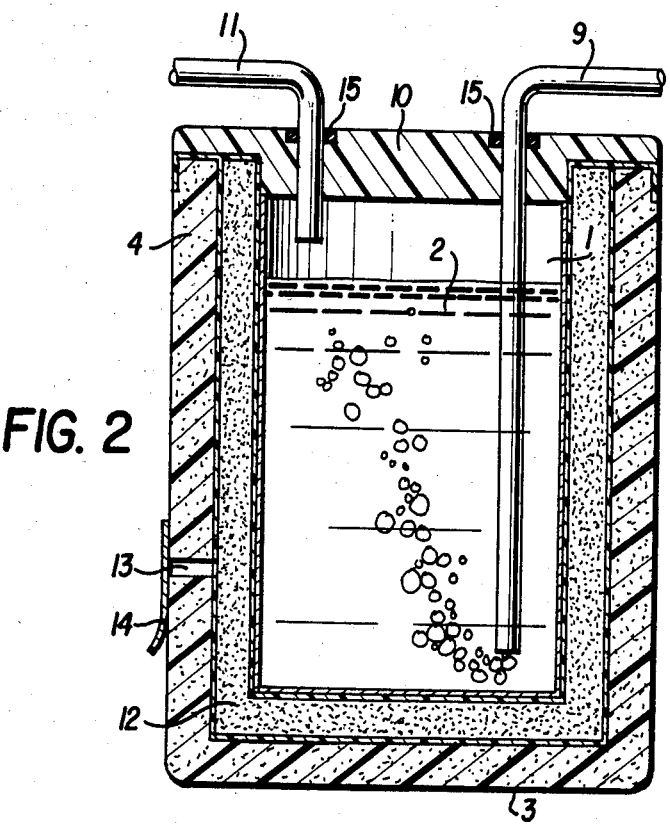
FIG. 2 is a side view of a second embodiment of the invention.

FIG. 2 shows a variation of the above-described embodiment in which air reacts with a dry chemical to produce heat. In this embodiment, only one compartment 12 is provided in outer container 3 which holds the reactive chemical. Compartment 12 communicates with the external atmosphere by means of communication passage(s) 13 which are sealed closed during storage of the container, for instance by resealable tape 14. An air permeable membrane may be interposed between the inner wall of the container and the reactive chemical to prevent leakage of the chemical through the communication passage(s). When heating is desired, the communication passages 13 are opened to the atmosphere, for instance by peeling back the tape 14, thus allowing air to enter the compartment 12 and mix and react with the chemical therein. In this embodiment, the outer container 3 is reusable until all of the chemical in compartment 12 is reacted, since the supply of air from the atmosphere can be cut off at will simply by re-sealing the passages 13. The reactive chemical in this embodiment may be a mixture of iron powder, sodium chloride and activated charcoal, as is used in a hand warmer device presently being sold under the trademark "Handy-Heat". As this embodiment is sensitive to the amount of oxygen in the ambient air, one should avoid using this system in areas where the air is particularly oxygen enriched.

Figure 3:
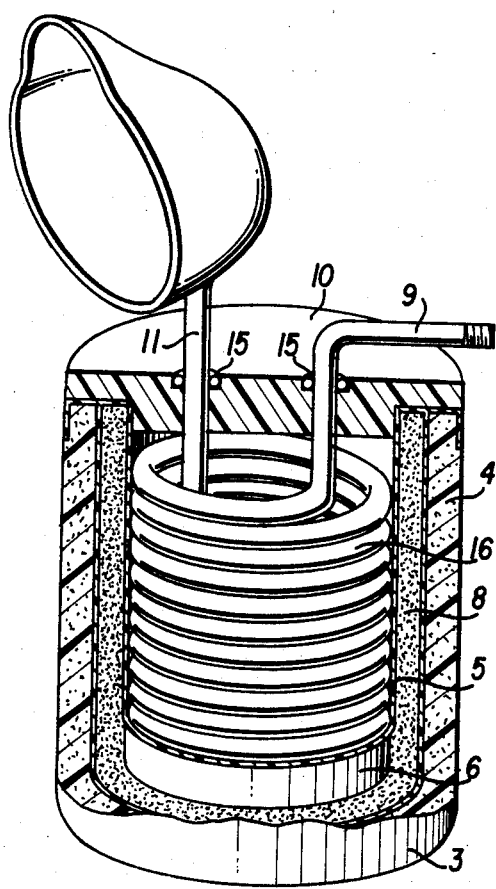
FIGS. 3 and 4 are perspective views of two further embodiments of the invention.
Figure 4:
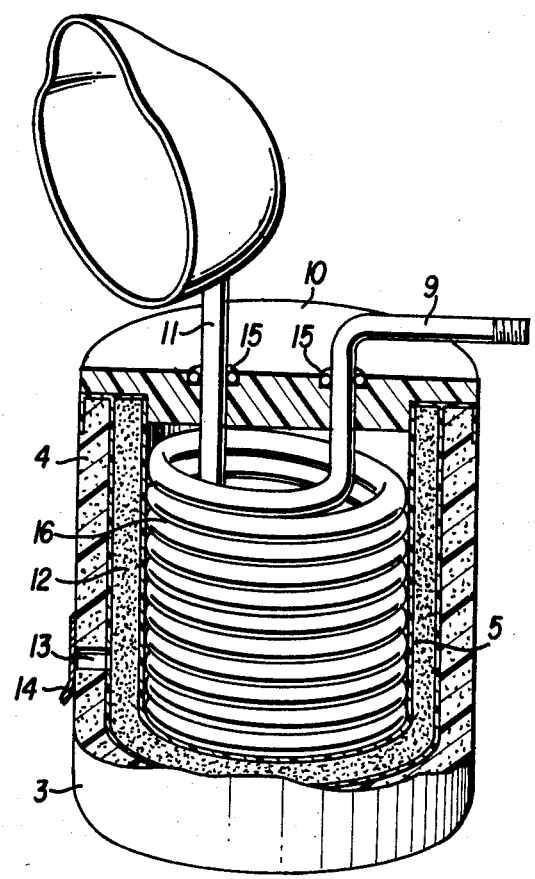

In another embodiment of the present invention shown in FIG. 3, the therapeutic gas is fed through the apparatus without humidification. In this embodiment, coiled tubing 16 is used in place of the inner container 1. This coiled tubing can be made of an inexpensive material integral with the outer container 3, in which case the frangible membrane would be broken by means of pressure against a non-rigid portion of the outer surface of that container; or the coiled tubing can be separate and insertable in a fashion similar to the insertion of the inner container 1 in the embodiment of FIG. 1. The coiled tubing transmits heat from the exothermic reaction to the therapeutic gas. FIG. 4 shows a similar non-humidified gas apparatus with a heating means corresponding to that used in the embodiment of FIG. 2. In these embodiments, a lid on container 3 is not necessary, although it would be useful to increase heating efficiency.

Figure 5:
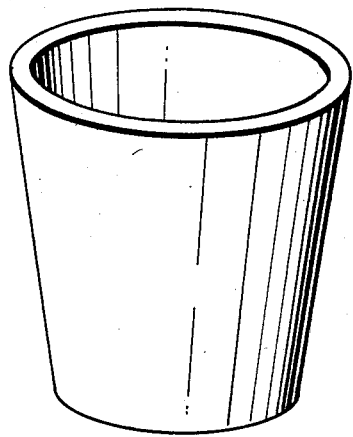
FIGS. 5 and 6 are perspective views of two embodiments of an outer container according to the invention.

FIG. 5 shows a preferred variation of container 3 which is frusto-conical in shape, resulting in easy stackability of the stored containers, thus improving their portability. The internal container 1 would be correspondingly shaped. Furthermore, although the round cross-sectional shape is preferred, it is not necessary and other shapes are quite acceptable. For instance, rectangular cross sectional shapes may be desirable to conform to certain imposed storage requirements.

Figure 6:
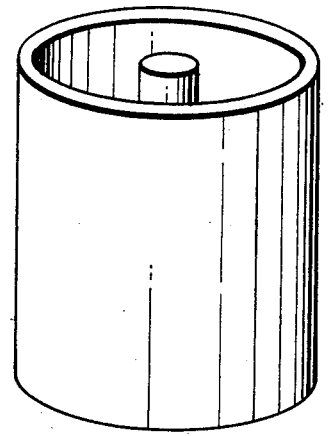

In the embodiments of FIGS. 3 and 4, a central core of container 3 holding the reactive chemical can also be added which extends upwards through the axial space surrounded by the coiled tubing, as shown in FIG. 6. This provides further heating capability and a longer life for the reusable type device although adding somewhat to the cost of construction.

It is clear that other variations on this invention could be made by those of skill in the art without departing from the spirit of the invention and the scope of the appended claims. For instance, the component materials, the shape of the tubing within container 3, the type of attachments, etc., may be varied according to desired features of this invention in light of the teachings herein.

What is claimed is:

1. A hand-held portable medical gas warming apparatus for treating and preventing hypothermia, said apparatus comprising:
   a disposable outer container means having a heat insulative lightweight outer wall, a rigid inner wall and a self-contained heating means comprising at least one exothermically reactive chemical substance disposed between said inner and outer walls;
   inner cavity means substantially surrounded by said heating means through which therapeutic respiratory gases may be passed and simultaneously warmed by an exothermic reaction in said heating means without causing communication other than heat transfer between said heating means and said gases;
   inlet means for introducing said gases into said cavity; and outlet means for removing said gases from said cavity after warming and for transmitting said warmed gases to a patient.

2. A device according to claim 1 in which said outer container further comprises two compartments between said inner and outer walls and separated by a frangible membrane, said two compartments each containing a different chemical substance, said two chemical substances selected so as to produce an exothermic reaction when mixed.

3. A device according to claim 2 wherein said outer container is constructed of inexpensive, disposable materials.

4. A device according to claim 2 wherein said two chemical substances are chosen from among compounds which produce a heat of reaction of approximately 38°–43° C. when mixed.

5. A device according to claim 2, further comprising a watertight inner container for holding a fluid, wherein said inlet means extend to a short distance above the bottom of said inner container and said outlet means open into said inner container near the top thereof;
said inner container being sealable from entry or exit of gases except through said inlet means and outlet means.

6. A device according to claim 2 wherein said inlet and outlet means are gas-tightly connected by a spiral tubing with a large surface area located within said inner cavity.

7. A device according to claim 2 in which said outer container is of a frusto-conical shape.

8. A device according to claim 1 wherein said outer container is constructed of inexpensive, disposable materials.

9. A device according to claim 1, further comprising a watertight inner container for holding a fluid, wherein said inlet means extend to a short distance above the bottom of said inner container and said outlet means open into said inner container near the top thereof;
said inner container being sealable from entry or exit of gases except through said inlet means and outlet means.

10. A device according to claim 9 in which said outer container is of a frusto-conical shape.

11. A device according to claim 1 in which said reactive substance exothermically reacts with air.

12. A device according to claim 11 in which said outer wall contains resealable air passages therethrough.

13. A device according to claim 11 wherein said inlet and outlet means are gas-tightly connected by a spiral tubing with a large surface are located within said inner cavity.

14. A device according to claim 1 in which said reactive substance exothermically reacts with air to produce a reaction temperature of approximately 38°–43° C.

15. A device according to claim 14 wherein said inlet and outlet means are gas-tightly connected by a spiral tubing with a large surface area located within said inner cavity.

16. A device according to claim 1 wherein said inlet and outlet means are gas-tightly connected by a spiral tubing with a large surface area located within said inner cavity.

17. A device according to claim 16 wherein said spiral tubing is so formed as to closely contact the inner wall of said outer container.

18. A device according to claim 16 wherein said inner wall of said outer container further comprises an upwardly extending cylindrical portion centered on the bottom of said outer container, said upwardly extending portion having an external diameter slightly smaller than the internal diameter of said spiral tubing.

19. A device according to claim 1 in which said outer container is of a frusto-conical shape.

20. A device according to claim 1 wherein said outlet means includes an oxygen delivery mask.

21. A device according to claim 1 in which said inner cavity comprises spiral tubing gas-tightly connecting said inlet means and outlet means.

22. A hand-held portable medical gas warming apparatus for treating and preventing hypothermia, said apparatus comprising:
a disposable outer container means having a heat insulative lightweight outer wall, a rigid inner wall and a self-contained heating means comprising at least one exothermically reactive chemical substance disposed between said inner and outer walls;
inner cavity means substantially surrounded by said heating means through which therapeutic respiratory gases may be passed and simultaneously warmed by an exothermic reaction in said heating means, said outer container and inner cavity preventing communication other than heat transfer between said gases and said heating means;
inlet means for introducing said gases into said cavity; and
outlet means for removing said gases from said cavity after warming and for transmitting said warmed gases to a patient.

* * * * *